United States Patent
Lewis et al.

(10) Patent No.: US 10,222,327 B2
(45) Date of Patent: Mar. 5, 2019

(54) METHOD OF LOCATING BURIED LEAD WATER PIPES USING INFRARED ANALYSIS

(71) Applicants: William T Lewis, Chesterfield, MO (US); Linda L Lewis, Chesterfield, MO (US)

(72) Inventors: William T Lewis, Chesterfield, MO (US); Linda L Lewis, Chesterfield, MO (US)

(*) Notice: Subject to any disclaimer, the term of this patent is extended or adjusted under 35 U.S.C. 154(b) by 0 days.

(21) Appl. No.: 15/806,296

(22) Filed: Nov. 7, 2017

(65) Prior Publication Data

US 2018/0136121 A1    May 17, 2018

Related U.S. Application Data

(60) Provisional application No. 62/421,110, filed on Nov. 11, 2016.

(51) Int. Cl.
  *G01N 21/3563* (2014.01)
  *G01N 33/20* (2006.01)

(52) U.S. Cl.
  CPC ......... *G01N 21/3563* (2013.01); *G01N 33/20* (2013.01)

(58) Field of Classification Search
  CPC ............. G01N 21/314; G01N 21/3554; G01N 21/3563; G01N 33/0011; G01N 33/20
  See application file for complete search history.

(56) References Cited

U.S. PATENT DOCUMENTS

| | | | | |
|---|---|---|---|---|
| 2001/0042834 A1* | 11/2001 | Kenway | ................. | G01N 25/72 250/341.6 |
| 2008/0265162 A1* | 10/2008 | Hamrelius | ................ | G01J 5/10 250/330 |
| 2010/0025582 A1* | 2/2010 | Weil | ....................... | G01N 25/72 250/332 |
| 2011/0292677 A1* | 12/2011 | Rossiter | ................. | G01N 30/74 362/580 |
| 2015/0100267 A1* | 4/2015 | Mischke | ................... | G01J 5/10 702/130 |
| 2016/0349174 A1* | 12/2016 | Washburn | ............ | G01N 21/272 |

* cited by examiner

*Primary Examiner* — David P Porta
*Assistant Examiner* — Fani Boosalis
(74) *Attorney, Agent, or Firm* — CreatiVenture Law; Linda L. Lewis

(57) ABSTRACT

A method of locating lead goose neck pipes connected between a water main and a water service line buried under a surface comprising, using infrared (IR) photography to scan the surface above the buried pipes; wherein the water main and water service lines are constructed of a metal having a higher thermal conductivity than lead; and determining the presence of lead by differences in surface temperatures of the lead pipe and the water main and/or the service line as indicated by the infrared photography.

2 Claims, 14 Drawing Sheets

METHOD OF LOCATING BURIED LEAD WATER PIPES USING INFRARED ANALYSIS

CROSS-REFERENCE TO RELATED APPLICATIONS

This application claims the benefit of provisional patent application No. 62/421,110 filed on Nov. 11, 2016, which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to non-destructive and remote infrared testing, and more particularly to infrared testing to locate buried lead water pipes, particularly lead gooseneck pipes connecting a water main to a water service line without excavating the pipes.

Related Art

The EPA started regulating lead in tap water in 1991 in the wake of numerous health studies that linked lead in drinking water to cases of severely elevated lead levels in the blood of consumers. Water companies generally try to keep lead levels low by controlling water chemistry; water that is too corrosive can liberate more lead from pipes and solder. But if tap water lead levels continue to exceed the action level of 15 ppb after corrosion, control is implemented. The federal Lead and Copper Rule (LCR) then requires water utility companies to begin replacing lead service lines. Determining the location of lead service lines can be done by examining the pipe entering the house through the basement wall. New service lines are typically made of copper pipe.

In Tacoma, Wash., between 1900 and 1940, short pieces of lead pipe were sometimes used to connect the water main to customers' service lines. These lead pipes could be easily bent and allowed for a flexible connection between the rigid pipes. These short connecting pipes are called "gooseneck" pipes. Over time, Tacoma Water has removed an estimated 30,000 of the lead goosenecks while replacing old service connections. Lead gooseneck pipes are difficult to locate because they are directly connected to the water main which is often buried under the street or sidewalk.

Although it is believed that the majority of the Tacoma lead goosenecks have been removed, there are still hundreds of old service connections which have not been located. When these lines were installed, details of where lead goosenecks were installed were not recorded. It is estimated that there may be up to 1,200 service connections that may have lead goosenecks. Since they are buried underground near the main, lead gooseneck locations are challenging to confirm. The established way of confirming lead gooseneck locations is excavation.

In Ann Arbor, Mich., a similar situation occurred. Ann Arbor has no records of lead pipes for water or sanitary sewer mains within its system. However, the gooseneck connections between the service pipe and the water main were made with a piece of lead pipe about ½" in diameter and about 2' long.

At one time there were thousands of "goose necks" within the Ann Arbor system, however today only 118 of these connections remain. As streets are resurfaced or repaved, the city's portion of the galvanized water services are replaced with copper. Copper is flexible and does not require lead goose necks, which are removed when replaced.

Lead goose neck water pipes also need to be located in East Lansing, Mich., Pennsylvania and Seattle, Wash.

Infrared technology has been used to detect pipes buried underground. When solar radiation falls on any surface of material, part of this radiation will be reflected from the surface and the rest will be absorbed. The energy generated by the absorbed radiation will increase the temperature of the surface of the material. The difference in temperature between the surface and the material underneath will create heat flow from the hot part to the cold part. The rate of heat flow depends on the thermal conductivity (k) of the material and the amount of temperature difference. It is well known that heat transfers between bodies by conduction, convection and radiation. Heat is the energy that flows from the hotter body to the cooler one. For a buried pipe, heat transfers from the surface above the pipe to the pipe and vice versa based on which is colder and which is hotter.

Typically, underground pipe mapping is done when the surface temperature has equilibrated, allowing consistent readings that allows the location of pipes, leaks and voids. If this measuring is done at night, the surface is cooler and the metal pipes are hotter, resulting on a hot spot over the pipe being measured using an IR camera. This hot spot is a hot spot when compared to surrounding surfaces, but not over the pipe. Conversely, if the measurement is made during the middle of the day, the surface is hot and the pipe is cooler, resulting in a cool spot being measured using an IR camera. The cool spot is cooler than the surrounding surfaces that are not over the pipe. The surrounding surfaces not over the pipe are referred to as remote surfaces. However, no studies have been made to determine if there is a discernable difference in the IR appearance of different metals, in particular lead versus other metals such as cast iron or copper.

The thermal conductivity (k) of lead (35 W/mK) is much lower than cast iron (47-80 W/mK) or copper (386 W/mK). This indicates that in periods of thermal transition, heating up or cooling down, the different metals would give a different thermal signature. In other words, under increasing heat, such as after sunrise, the lead, being slow to conduct heat away from its surface, would have a hotter surface than cast iron or copper. It would appear as a hot spot when compared to remote surfaces. The cast iron or copper would be a heat sink and transmit the heat along the pipe and away from the surface showing a cool spot. The opposite effects would occur under cooling conditions, such as after sunset. The same differences in thermal signature would be present during equilibrium (non-changing conditions) of lead versus other metals.

SUMMARY OF THE INVENTION

A method of locating lead goose neck pipes connected between a water main and a water service line buried under a surface comprising, using infrared (IR) photography to scan the surface above the buried pipes; wherein the water main and water service lines are constructed of a metal having a higher thermal conductivity than lead; and determining the presence of lead by differences in surface temperatures of the lead pipe and the water main and/or the service line as indicated by the infrared photography.

A method of determining the presence of buried metallic lead pipe, wherein above the pipe is a buried pipe surface and remote from the pipe is a remote from pipe surface, comprising:

scanning the buried pipe surface using an IR camera;

scanning the remote from the pipe surface using an IR camera;

determining whether the surface above the pipe is hotter or colder than the surrounding surface;

determining whether the ambient temperature is increasing or decreasing;

wherein for increasing ambient temperature, a hotter temperature indicates that the pipe is lead and a colder temperature indicates that the pipe is not lead; and wherein for decreasing ambient temperature, a hotter temperature indicates that the pipe is not lead and a colder temperature indicates that the pipe is lead.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
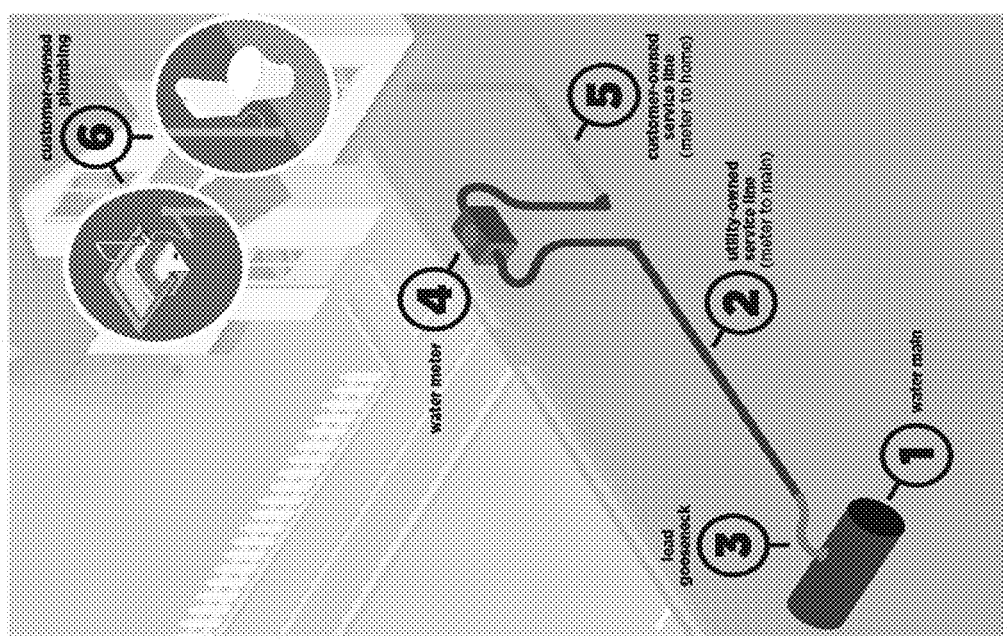
FIG. 1 is a diagram of a water system.

The following description of the preferred embodiment(s) is merely exemplary in nature and is in no way intended to limit the invention, its application, or uses. FIG. 1 shows the following:

1: Water Main—The water main brings treated water or groundwater wells to customers' pipes.

2: Utility-Owned Service Line (meter to main)—The utility-owned service line is the pipe that connects the water main in the street to customer household plumbing.

3: Lead Gooseneck—The lead gooseneck is a short section of pipe that connects some water mains to service lines. The gooseneck is utility owned.

4: Water Meter—The water meter measures and registers the amount of water that passes from the utility-owned service line to the customer-owned service line.

5: Customer-Owned Service Line (meter to home)—The customer is responsible for customer-owned service line and plumbing after the meter and into the home.

6: Customer-Owned Plumbing—The customer is responsible for customer-owned service line and plumbing after the meter and into the home.

Examples of the Invention

Test 1

Test 1 Setup

Figure 2:
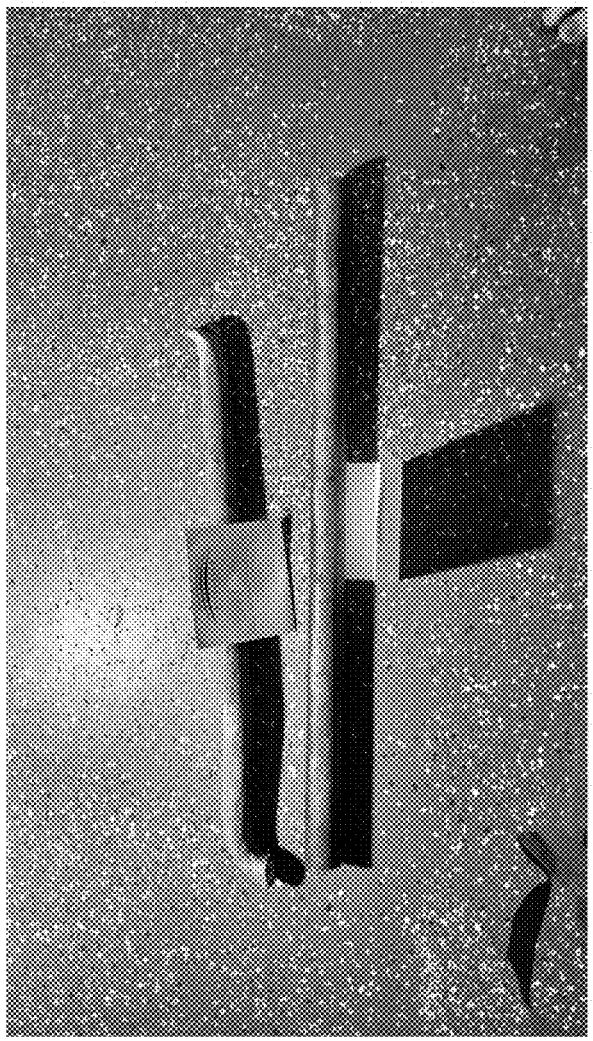
FIG. 2 shows a lead pipe and an iron pipe.
Figure 3B:
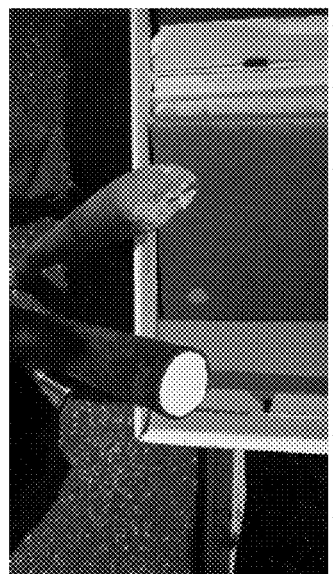
FIGS. 3A and 3B shows plugs on the ends of both pipes.
Figure 3A:
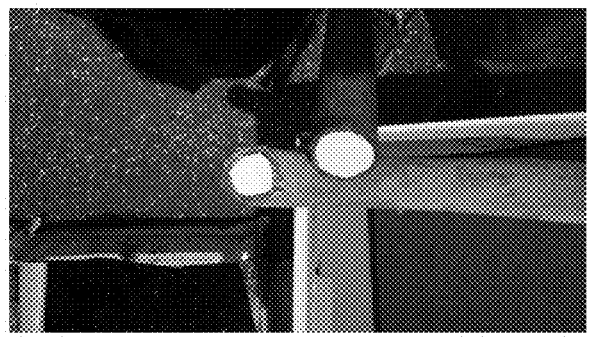

Two pipes, one iron and one lead, were used to simulate buried pipes and are shown in FIGS. 2, 3A and 3B. The lead pipe was 5 pounds, 27 inches long, with an outer diameter of 1.5 inches, and the iron was 4.5 pounds, 31.5 inches long, with an outer diameter of about 1.62 inches. For consistency and simplicity, both pipes were empty. This was ensured by having plugs on the two open ends of the iron pipe and the one on the lead pipe. The physical differences between the two pipes were that the iron was slightly longer, had a larger inner and outer diameter, and had a thinner wall thickness.

Figure 4:
FIG. 4 shows the assembled box with black trash bag lining.
Figure 5:
FIG. 5 shows the assembled box with the lining adhered.

As shown in FIGS. 4 and 5, a device was assembled to both house and insulate the pipes from two file boxes and black plastic bags. First a 2" deep layer of potting soil was laid and the two pipes were laid on it. Potting soil was then increased around the pipes and above them till the iron pipe was 2" below the surface.

Figure 6B:
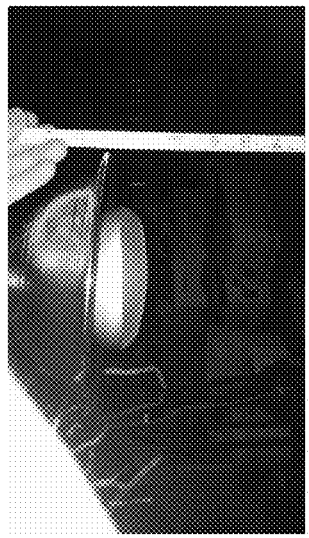
FIGS. 6A and 6B show a heat lamp setup.
Figure 6A:

As shown in FIGS. 6A and 6B, a single heat lamp was hung 23" above the potting soil surface to create thermal transition and to simulate a rising sun. The bulb used in the heat lamp was a 125 W Sylvania Brooder Heat Lamp BR40 bulb. It was hung with a single rope piece and had a simple on/off switch to quickly and easily control when light was applied. There was no graduated control of the light intensity, due to simplicity of design of the test.

Test 1 Method

The test was started before sunrise to use the natural heating of the day to the advantage of the test. The test started at ~5:30 am where IR pictures were taken of the setup without the heat lamp being on. This was done at 6:10 am to ensure that there was thermal equilibrium in the test setup before starting. From there, the lamp was turned on and the test setup was photographed with the IR camera approximately every thirty minutes and the emissivity variations were observed. Specifications for the IR camera are given below.

Test 1 Results

Figure 7:
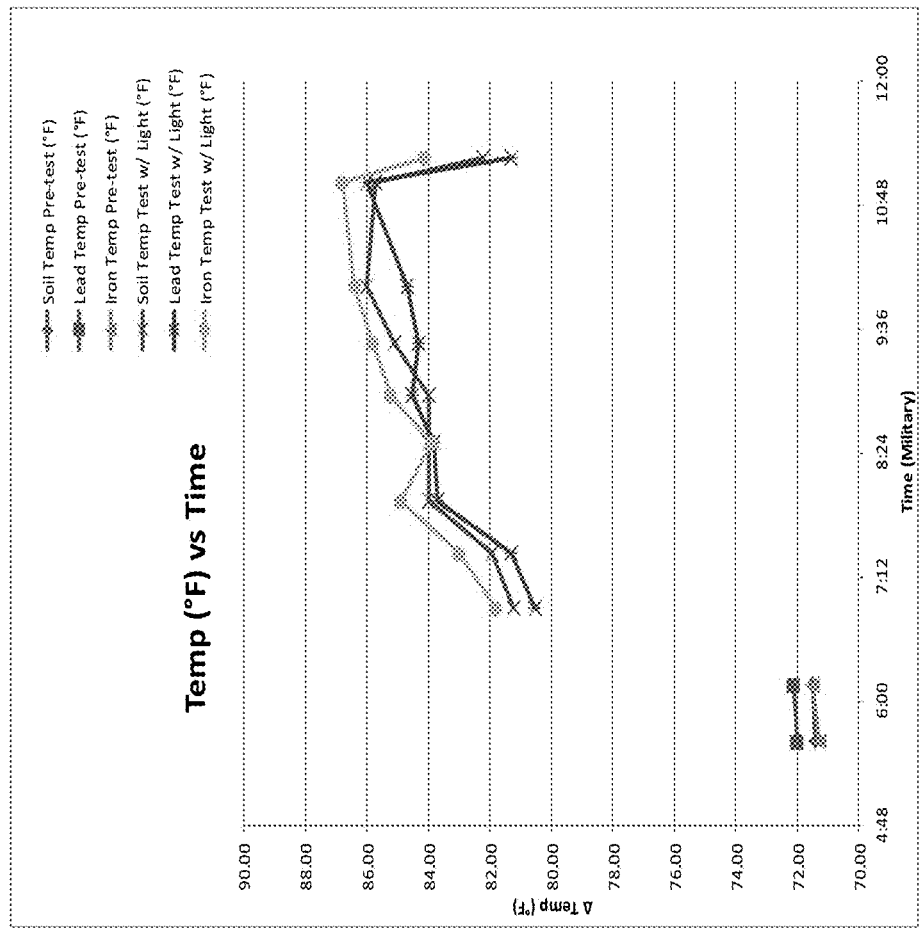
FIG. 7 shows Test 1 results, Time vs Temperature graph.
Figure 8:
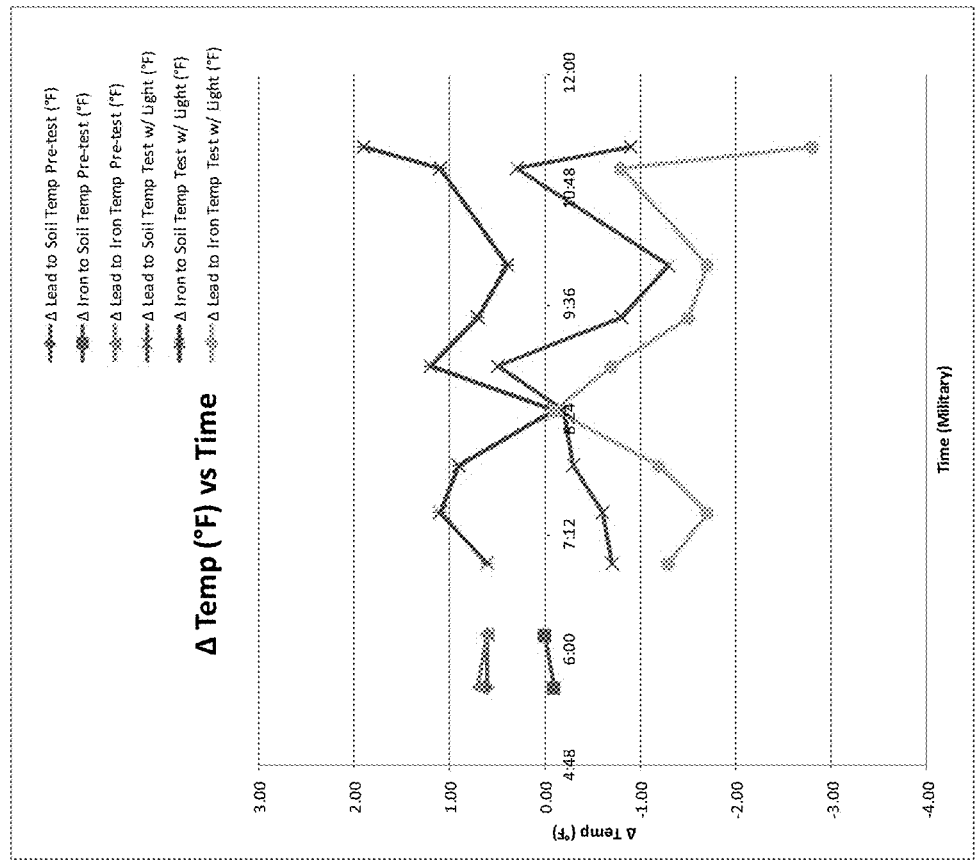
FIG. 8 show Test 1 results, Time vs Temperature Differential graph.
Figure 9B:
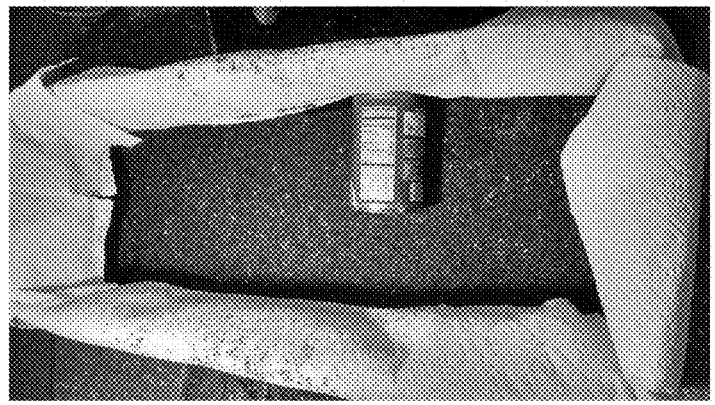
FIGS. 9A and 9B show the laying and compacting of the first layer of soil.
Figure 9A:
Figure 10B:
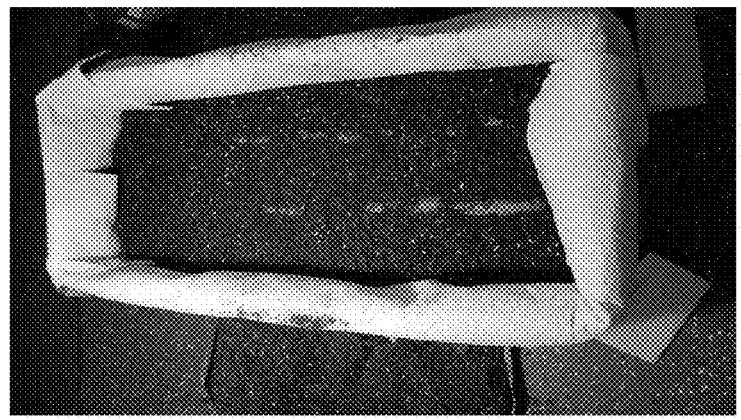
FIGS. 10A and 10B show the pipes laid and buried.
Figure 10A:
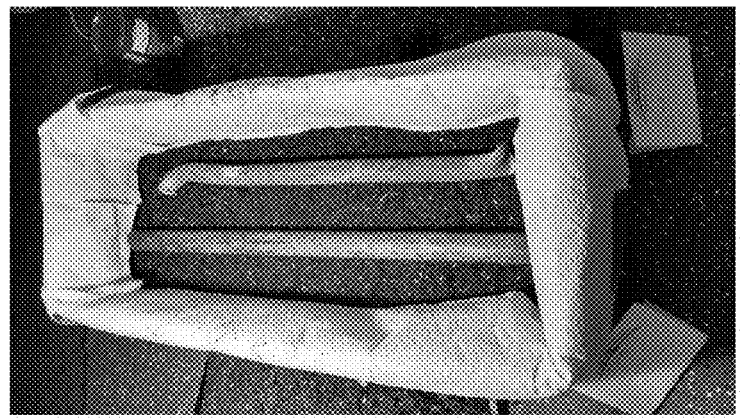
Figure 14:
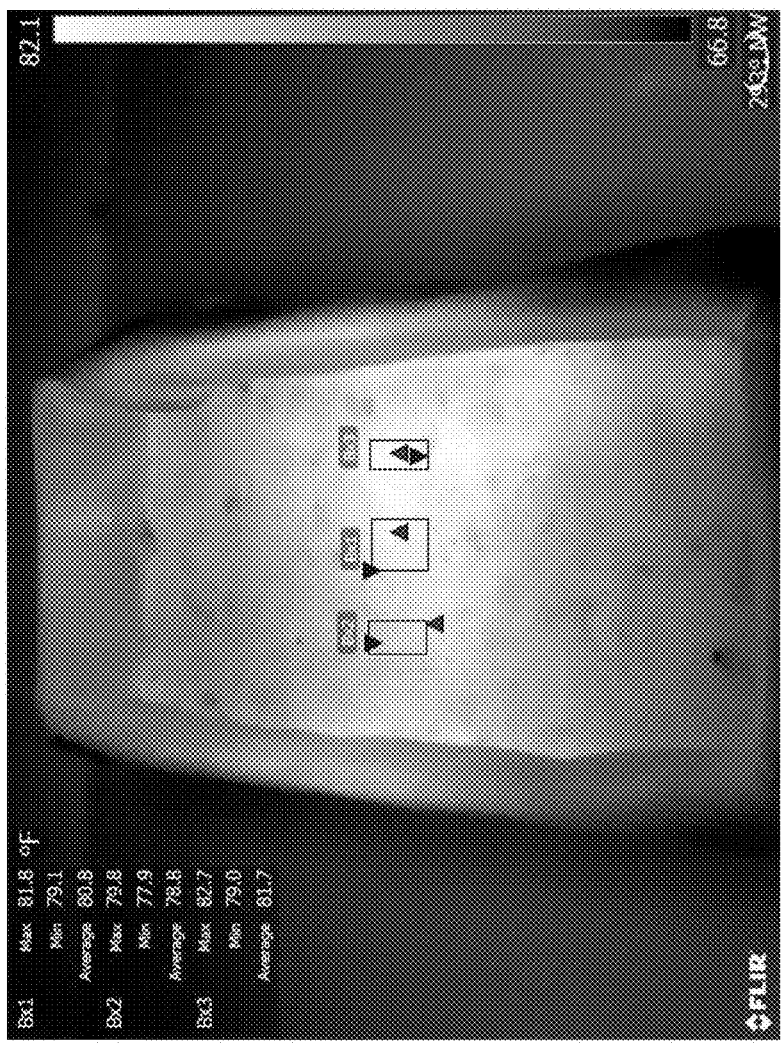
FIG. 14 shows the IR Image at the Height of Emissivity Difference for Test 3.

The primary focus of investigation of IR-EPA is to compare the emissivity change (converted into an estimated temperature change). Three areas on the surface of the soil were of interest, and are marked with a box, Bx1, Bx2 and Bx3. Starting on the left, the Bx1 is the surface above the location of the iron pipe and is labeled the Iron Temp. The middle, Bx2 is the surface remote from the iron pipe and the lead pipe location, and is labeled the Soil Temp. The right, Bx3 is the surface above the lead pipe and is labeled the Lead Temp. FIG. 14 shows the IR Image at the Height of Emissivity Difference and is an example of the IR images taken. In FIG. 7, the highest calculated temperature in the three areas of interest were graphed in relation to time. In FIG. 8, the differences of the three temperatures were computed and graphed in relation to time. It is notable that it was assumed (for the first test ONLY) that the emissivity would be the same before and after the heat lamp was turned on and subsequently no picture was taken of the setup with the heat lamp at 6:10 am.

From these initial results, there was not solid conclusion to be made due to the excessive scatter in the data. Also, it was speculated that the looseness of the soil and residual moisture in the soil was interfering with the heat and subsequent IR camera images. This was particularly notable in the jump of non-heated to heated surface temperature. If the soil was loose, it would act as an insulator and the heat effect would not penetrate to the buried pipes.

Test 2

In Test 2, the pipes were directly heated unburied. The idea was to simply remove the variable of the loose soil. The pipes were removed from the soil and placed in a conventional oven. The oven was pre-heated to 200 F° and both pipes were put inside. Due to the size constraints of the oven, the pipes were laid at an angle and the oven door was left open, which turned the heaters in the oven off. The temperature as a function of time was taken an equidistance (approximately 4" into the oven from the entrance of the oven).

TABLE 1

Test 2

| Time versus Temperature for Lead and Iron Pipes Time (minutes) | Lead Pipe Temperature (° F.) | Δ Temperature Lead Pipe | Iron Pipe Temperature (° F.) | Δ Temperature Iron Pipe |
|---|---|---|---|---|
| ~5 | 113 | | 103 | |
| ~25 | 99 | −14 | 97 | −6 |
| ~35 | 91 | −8 | 92-93 | −4, −5 |

The first five minutes were given to allow the pipes to initial absorb heat and then the fall in emissivity was observed to see what the difference was between the two pipes. It was observed that the lead emissivity was initially higher than the iron, but it then fell much faster in relation.

When initially heated, the iron pipe with its higher thermal conductivity would absorb and disperse heat into the pipe, creating a relatively lower surface temperature while absorbing the heat. On the other hand, the lead pipe would absorb heat on its surface but disperse it slowly resulting in the surface temperature being higher. The IR camera only measures the surface effect.

It should be noted that a thermal equilibrium was not allowed and, indeed, there was probably temperature differentials in the pipes themselves. With that in mind, the iron pipe was able to both store more heat due to pulling it into the material of the pipe as opposed to the lead pipe which kept the heat nearer to its surface. This explains why the emissivity of the lead pipe fell much faster than the iron pipe as it quickly dissipated its surface heat and was slower to bring to the surface any heat that it stored during the heat up. The iron pipe in contrast had a more heat to draw from and its thermal conductivity gave easier access for the heat to come back to its surface.

Another consideration is the difference in pipe thickness between the lead and iron. It is speculated that this had a minimal effect if any as the pipes were not allowed to reach thermal equilibrium at the heated state and therefore the temperature change may not have even had a chance to fully start propagating throughout either pipe. As such, the difference in pipe thickness was ignored for this side study.

With this new set of data, observations and conclusions, Test 3 setup was planned for burying the pipes.

Test 3

Test 3 Setup

As shown in FIGS. 9A, 9B, 10A and 10B, Test 3 was similar to the previous, except that the soil had been spread out to dry for three days. The dried soil was laid down in 1" layers and then compacted with a 40 oz. can (4" diameter by 6" height, 2½ pounds measured weight). Measuring the 1" was done with four small flags that were 1" high and laid on the surface prior to adding soil. The can was rolled over the layer of soil evenly with care given to not apply pressure downward (which would subsequently make the can effectively heavier and compact one area over another). This was performed three times before the pipes were put on the compacted surface. The measure depth at this time varied 2.50" near in the picture to 2.25" far.

Figure 11:
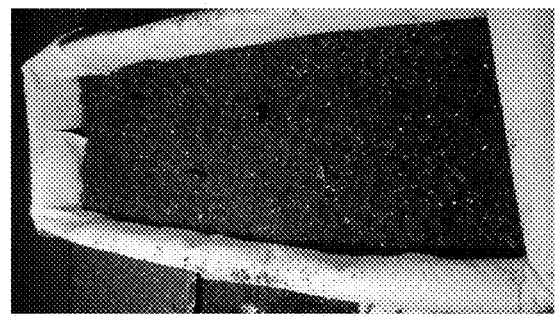
FIG. 11 shows the final layer added but not compacted.

Exceptions to this method are when the two pipes were laid in. Then soil was added until the pipes were almost completely covered. Then 1" of soil was added on top (measured from the top of the iron pipe) and the compact and addition process was continued. One more 1" layer of soil was then added and compacted as before. FIG. 11 shows the final layer added but not compacted.

The heat lamp was kept at the same height as before of 23". Paper towels were added to the side to prevent the black plastic from creating hot spots.

The final dimensions of the setup were measured at this time to include the variation in size due to the weight of the soil. The width of the box varied from 12" at the near and far ends and 12½" in the middle. The total height of the setup was 10½". The final depth of the soil was 6" (the measured distance from the top of the setup to the soil was 4½"). The length of the interior of the box was 34 inches.

Test 3 Method

The test method used was the same as the Test 1 except that the IR pictures were taken approximately every hour as opposed to every 30 minutes during the heat up period. Additionally, IR pictures were taken after the cooldown period had begun every 30 minutes until a relative stability had been achieved.

Test 3 Results

Figure 12:
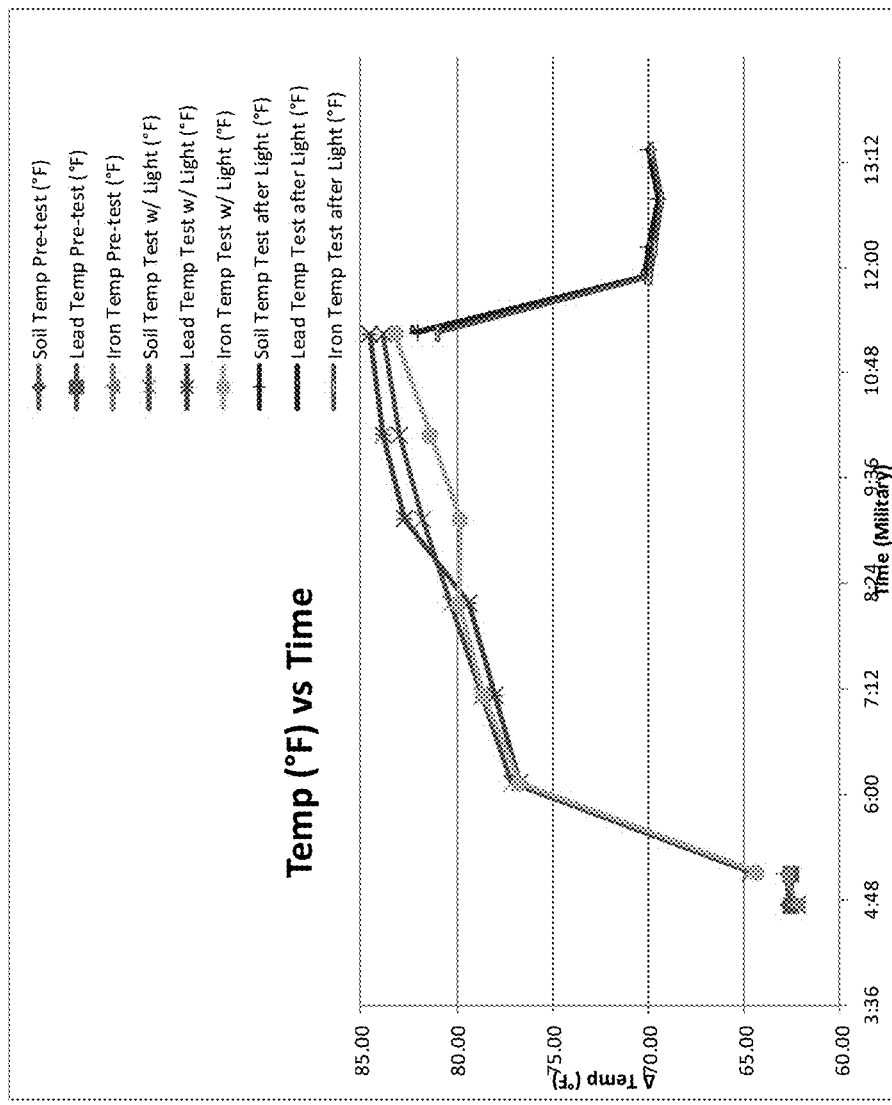
FIG. 12 shows Test 3 results, Time vs Temperature graph.
Figure 13:
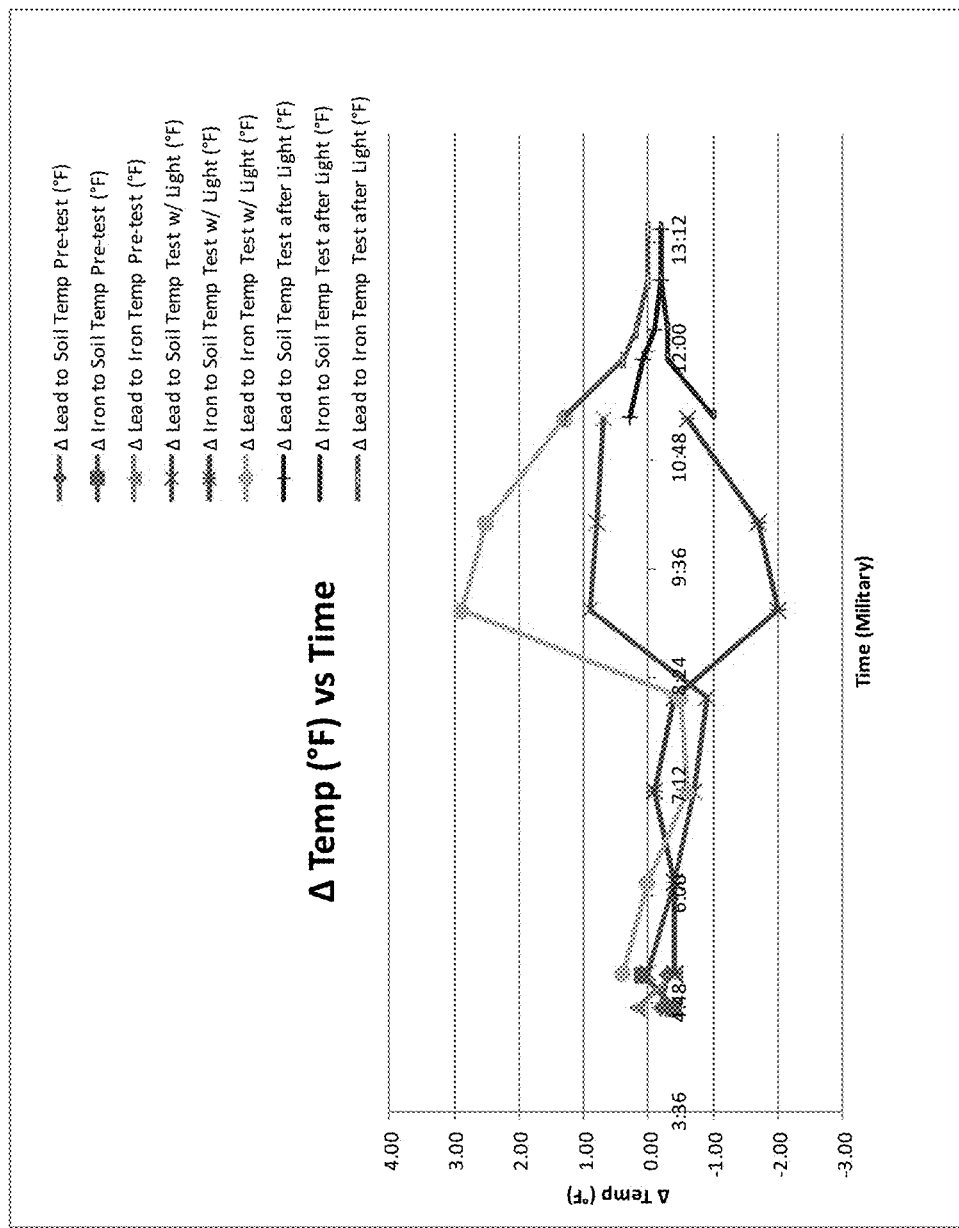
FIG. 13 shows Test 3 results, Time vs Temperature Differential graph.

The third test resulted in much more uniform heat signatures from the soil. The results are plotted and calculated in the same way as the Test 1 Results and are shown in FIGS. 12 and 13.

In this case, there is a clear difference in temperature, showing that the lead pipe results in a warmer emissivity signature than the iron pipe. Additionally, there was a clear image of higher measured emissivity over the lead pipe in comparison to the iron as shown in FIG. 14.

CONCLUSION

Referring to the results of the Third Test, it is entirely possible to detect a difference between the rate of emissivity change of iron and lead during a temperature change in the environment. That said, there are other considerations to investigate if a thorough investigation is desired.

Typically, during the morning (as per the simulation), metal pipes act as heat sinks, creating a cool spot on the ground above the pipes (and vice versa during sundown). However, it was observed that the soil over the lead pipe appeared to be a warm spot. In fact, the data shows a cool spot over the iron pipe and a warm spot over the lead pipe.

This may be due to the lead being a poor conductor of heat and the surface of the lead pipe quickly matching the temperature of the surrounding soil. It would also provide poor heat conduction from the surface of the soil down, acting like a thermal insulator in the ground. This would cause a hot spot as the soil would effectively not be able to direct heat away as fast as surrounding more continuous soil. In other words, heat would build up above the lead pipe.

To consider this condition, the thermal conductivity of the soil in addition to the lead and iron must be considered. If the soil's thermal conductivity is significantly higher than the lead's, then the lead may be acting as a thermal insulator in the soil.

The effects of pipe diameter, wall thickness, and contents should also be considered when evaluating for field applications. Additionally, for water piping, it should be considered whether there is a high, low, or no flow condition, and the temperature of the fluid.

For a practical application, it should be determined at approximately what time(s) the difference in emissivity would be greatest. For Test Three, the maximum difference appears at about 4 hours after the heat lamp is applied. This would give an ideal time for conducting investigations. This could be address either by straight field study and imperial analysis or by determining when applying an external heat source would result in the greatest emissivity difference and determining the hour at which that would occur.

List of Specifications and Settings for the IR Camera

The camera used to take IR images was the FLIR T650sc 2.1

25° lens
Serial #55906755
Part #55904-7823
Temperature range: −40 to 302° F.
Temperature accuracy used: ±0.05° F.
The camera settings used were:

| Emissivity | ε = 0.95 |
| Reflected Temperature | 68° F. |
| Relative Humidity | 50% |
| Atmospheric Temperature | 68° F. |
| Object Distance | 1 meter |
| External IR Window Compensator | OFF |

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method of locating lead goose neck pipes connected between a water main and a water service line buried under a surface comprising, photographing the surface above the buried pipes during a period of thermal transition; wherein the water main and the water service lines are constructed of a metal having a higher thermal conductivity than lead; and determining the presence of lead by differences in surface temperatures of the lead pipe and the water main and/or the service line as indicated by the infrared photography.

2. A method of determining the presence of buried metallic lead pipe, wherein above the pipe is a buried pipe surface and remote from the pipe is a remote from pipe surface, comprising:
    scanning the buried pipe surface using an IR camera;
    scanning the remote from the pipe surface using an IR camera;
    determining whether the surface above the pipe is hotter or colder than the surrounding surface;
    determining whether the ambient temperature is increasing or decreasing;
    wherein for increasing ambient temperature, a hotter temperature indicates that the pipe is lead and a colder temperature indicates that the pipe is not lead; and
    wherein for decreasing ambient temperature, a hotter temperature indicates that the pipe is not lead and a colder temperature indicates that the pipe is lead.

* * * * *